United States Patent [19]
Fitzpatrick et al.

[11] Patent Number: 6,110,473
[45] Date of Patent: *Aug. 29, 2000

[54] EMULSION COMPRISING A GELLED ANIONIC HYDROCOLLOID AQUEOUS OUTER PHASE, A NON-AQUEOUS INTERMEDIATE PHASE AND AN AQUEOUS INNER PHASE

[75] Inventors: John Fitzpatrick, Treelands; Adrian Mellor, Southwater, both of United Kingdom

[73] Assignee: Monsanto P.L.C., Buckinghamshire, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/737,449
[22] PCT Filed: May 17, 1995
[86] PCT No.: PCT/EP95/01892
  § 371 Date: May 7, 1997
  § 102(e) Date: May 7, 1997
[87] PCT Pub. No.: WO95/31967
  PCT Pub. Date: Nov. 30, 1995

[30] Foreign Application Priority Data

May 19, 1994 [GB] United Kingdom ................... 9410092

[51] Int. Cl.$^7$ ........................................................ A61K 7/48
[52] U.S. Cl. .................. 424/401; 424/65; 424/66; 424/405; 424/409; 424/484; 514/847
[58] Field of Search ................... 424/401, 47, 65, 424/66, 67, 68, 78.03, DIG. 5, 489, 450, 405, 409, 484; 514/937, 938, 944, 847

[56] References Cited

PUBLICATIONS

I.W. Cottrell and P. Kovacs, "Alginates", *Handbook of Water–Soluble Gums,* Ed. R.L. Davidson, McGraw Hill, New York, NY, (1980).

*Primary Examiner*—Thurman K. Page
*Assistant Examiner*—R. Bawa
*Attorney, Agent, or Firm*—Fitzpatrick, Cella, Harper & Scinto

[57] ABSTRACT

The invention relates to an emulsion comprising an aqueous gelled outer phase, a non-aqueous intermediate phase and an inner phase containing an active ingredient incompatible with the gelled outer phase, wherein the outer phase comprises one or more anionic hydrocolloids in an amount of 0.1% to 5% by weight of the weight of the outer phase, the intermediate phase comprises an oil, and the inner phase containing the active ingredient is encapsulated by the intermediate phase. The emulsions are useful for the preparation of antiperspirants, sustained release drug formulations or personal hygiene products.

11 Claims, No Drawings

6,110,473

EMULSION COMPRISING A GELLED ANIONIC HYDROCOLLOID AQUEOUS OUTER PHASE, A NON-AQUEOUS INTERMEDIATE PHASE AND AN AQUEOUS INNER PHASE

BACKGROUND OF THE INVENTION

1. Field of the Invention

The present invention is concerned with an emulsion, a method of preparing the same and its use, and in particular an emulsion comprising a gelled outer phase having an active ingredient dispersed therein.

2. Description of the Related Art

Encapsulation of active ingredients in gels, such as gellan gum, is well known. For example, JP 62125850 discloses encapsulation of ingredients, such as food, oils, medicines and the like, within beads of gellan gum. In an example, a salad oil emulsion was added as 0.5 ml size drops to a 1% gellan gum solution. The resulting beads had a 0.35 mm thick skin and contained 0.3 ml of oil in each sphere.

U.S. Pat. No. 4,563,366 discloses a gelled food product which comprises a matrix containing at least one dispersed food ingredient which comprises vegetable, fruit, meat, fish, sugar, and/or milk.

GB2219803 discloses a gelling composition which comprises a blend of gellan, kappa-carrageenan and mannan. The gelling composition is useful as a gelling matrix in food products such as pet foods and the like.

JP 63267361 discloses a gel which can contain fragrances, microbicides, insecticides, and the like, in addition to a gelation agent selected from gellan gum, and its combination with carrageenan, gelatin, agar, locust bean gum, xanthan gum, carboxymethyl cellulose and the like.

Incorporation of certain active ingredients in gel matrices comprising anionic hydrocolloids, such as gellan gum, has however proved to be problematic due to the incompatibility of the active ingredients with the gels causing degredation or precipitation of the latter.

This incompatibility can be seen, for example, when aluminium chlorohydrate is blended with gellan gum in an attempt to prepare an antiperspirant, whereby undesirable precipitation of the gellan gum occurs. Similarly, the incompatibility of other cationic ingredients, such as cationic drugs (verapamil hydrochloride, chlorpheniramine maleate and the like) and cationic surfactants (such as benzalkonium chlorides and the like) with the above-mentioned anionic gel matrices has proven to be problematic.

SUMMARY OF THE INVENTION

The present invention alleviates the above problem, wherein active ingredients incompatible with a gel matrix can be incorporated therein without adversely affecting the properties of the gel.

According to the present invention there is provided an emulsion comprising an aqueous gelled outer phase, a non-aqueous intermediate phase and an aqueous inner phase containing an active ingredient incompatible with the gelled outer phase, wherein the inner phase containing the active ingredient is encapsulated by the intermediate phase.

DETAILED DESCRIPTION OF THE INVENTION

An emulsion according to the present invention therefore alleviates the problem described above, in that the intermediate phase separates the aqueous gelled outer phase from the active ingredients present in the aqueous inner phase.

Aptly the gelled outer phase comprises one or more gelled anionic hydrocolloids. A frequently employed hydrocolloid in the present invention is gellan gum, other suitable hydrocolloids being alginates, pectins, carrageenans, agar, locust bean gum and the like.

Gellan gum refers to the extracellular polysaccharide obtained by the aerobic fermentation of the microorganism, *Pseudomonas elodea*, in a suitable nutrient medium. Various forms of gellan gum are known e.g., native, deacetylated, deacetylated clarified, partially deacetylated, and partially deacetylated clarified.

It is preferred that the gellan gum employed in the present gel is a "low acetyl" gellan gum. As used herein, the term "low acetyl" denotes a level of acylation of the gellan gum of 0.3 to 0% by weight.

Various alginates useful in this invention are described in detail by I. W. Cottrell and P. Kovacs in "Alginates," as Chapter 2 of Davidson, ed., *Handbook of Water-Soluble Gums and Resins* (1980).

Alginates include "bioalgin" and "algal" alginate.

Biolalgin is microbially produced polysaccharides produced by both Pseudomonas and Azotobacter Strains as described, for example, in Jarman et al., U.S. Pat. No. 4,235,966. These alginates are polysaccharides consisting of a partially acetylated variable block copolymer of D-mannuronic and L-guluronic acid residues. iarman et al. state that the polysaccharide produced is similar to that produced from seaweed except that the molecule is partially acetylated.

The term "algal" alginate refers to naturally derived alginic acid and salts thereof. Naturally derived aiginic acid, derived primarily from kelp, is a commercially available product, e.g., KELACID™ (Kelco Div., formerly Merck & Co., Inc., now acquired by Monsanto Company). The salts include appropriate metal salts, e.g. alkali metal, alkaline earth metal, ammonium salts, and organic derivatives, e.g. alkylene glycol, propylene glycol and the like. The preferred salts are sodium, potassium, magnesium, ammonium and propylene glycol algal alginate. Most preferred herein are naturally derived algal sodium alginates, such as those sold commercially under the trademarks KELTEX, KELGIN and KELTONE™ by Kelco Division formerly Merck & Co., Inc., now Monsanto Company.

Pectins are plant cell wall polysaccharides comprising branched molecules that contain many negatively charged galacturonic acid residues. In view of their negative charge pectins are highly hydrated and readily bind to cations so as to be suitable for forming the gelled outer phase of the emulsion of the present invention.

Locust bean gum is an extract of the locust bean or carob, *Ceratonia siliqua*. It is commercially available and is often used as a stabilizer in foods such as ice cream, sausages, and cheese.

It is preferred that the anionic hydrocolloid is present in the gelled outer phase in an amount of 0.1 to 5% by weight, based on the weight of the outer phase, for example 0.25 to 2.5% by weight. In the case where an abradable gelled outer phase is required, for example in the case where the emulsion is for use as an antiperspirant, the hydrocolloid is typically present in an amount of 0.75 to 1.25% by weight, based on the weight of the outer phase. Alternatively for applications such as drug release systems, wherein the gelled phase is required to be erodible when in contact with body fluids, the anionic hydrocolloid is typically present in an amount of 0.5 to 0.6% by weight of the outer gelled phase.

Optionally the outer phase may, in some applications of the emulsion according to the present invention, such as for antiperspirants, body lotions and the like, further contain a fragrance which may typically be present in an amount of 0.75 to 1.25% by weigh, based on the weight of the outer phase. The outer phase may contain colourant if desired.

The gelled outer phase may also optionally contain a preservative, a preferred preservative being n-propyl p-hydroxybenzoate. The preservative is suitably employed in a minor amount, such as not greater than about 0.2% by weight of the gelled outer phase.

Optionally the gelled outer phase may further contain a biocide, typically present in an amount of 0.05 to 2.5% by weight based on the weight of the outer phase.

Suitably one or more surfactants are also included in the outer phase, examples of suitable surfactants comprising diethanolamide cetyl phosphate, polyoxyethylene castor oil, polyoxyethylene hydrogenated castor oil, polyoxyethylene triglycerides, polyoxyethylene lanolin, polyoxyethylene laurates, polyoxyethylene stearates and the like. Generally the surfactant is present in the outer phase at a level of 1 to 3% by weight, based on the weight of the outer phase, more preferably the surfactant is present at a level of 1.5 to 2.5% by weight, based on the weight of the outer phase.

The anionic hydrocolloid may typically be gelled by a suitable cation such as calcium, magnesium or the like.

In the case of such multivalent gelling cations, these cations are suitably provided by salts such as calcium chloride, magnesium chloride, calcium sulphate, magnesium sulphate and the like. The gelling multivalent cations are generally present in the outer phase of the emulsion at a level not greater than 0.05% by weight, based on the weight of the outer phase.

In the case where the anionic hydrocolloid comprises gellan gum, it is preferred that monovalent cations such as sodium, potassium and the like are employed to gel the gellan gum, potassium being particularly preferred. Aptly the monovalent cations are provided by a suitable salt such as sodium chloride, potassium chloride, trisodium citrate, tripotassium citrate and the like; in the case of potassium a preferred salt is tripotassium citrate.

Advantageously the gelling monovalent cations are present in the outer phase at a level not greater than 0.5% by weight, based on the weight of the outer phase.

In the case where monovalent gelling cations are employed it is preferred that the outer phase is essentially free of multivalent ions, such as calcium, magnesium or the like. The skilled worker will appreciate that it is most unusual to avoid gelling quantities of multivalent ions in this way since it is normal practice in the art to use multivalent ions to increase gel strength.

Desirably the non-aqueous intermediate phase comprises an oil phase which can comprise volatile silicone oils, petroleum, paraffin, or vegetable oil such as olive oil, arachis oil, castor oil, cottonseed or rapeseed oil or the like. In this way, there is provided by the present invention a triple phase emulsion of a water in oil emulsion dispersed in a water phase. A favoured oil phase in the present invention comprises a silicone oil, preferably a volatile silicone oil, although it is of course appreciated that the other above-mentioned oils can similarly be employed in the intermediate phase.

As hereinbefore described, an aim of the present invention is to encapsulate within a non-aqueous phase, an inner aqueous phase containing active ingredients incompatible with the gelled outer phase.

Aptly the active ingredients comprise cationic materials which are incompatible with anionic hydrocolloid gels in that the former would effect degradation or precipitation of the latter.

Examples of such cationic materials include polyvalent metal ions, typically present as salts such as aluminium and/or zirconium salts, typically aluminium chlorohydrate, aluminium-zirconium chlorohydrate and the like, cationic drugs such as verapamil hydrochloride, chloropheniramine maleate and the like, and cationic surfactants such as benzalkonium chlorides, cetyl trimethyl ammonium chloride, lauryl dimethyl ammonium chloride and the like.

It can be appreciated from the above range of active cationic ingredients that an emulsion according to the present invention has several applications.

In a first embodiment wherein the active cationic ingredient includes aluminium ions, the emulsion according to the present invention has applications as an antiperspirant; such antiperspirants containing aluminium ions were not previously prepared because of the incompatibility of aluminium containing materials with gels such as the anionic hydrocolloids suitable for use in the present invention.

In a second embodiment of the present invention wherein cationic drugs are present in the aqueous inner phase encapsulated by the intermediate oil phase, the emulsion of the present invention is useful as a sustained release drug system wherein the outer gel phase is slowly erodible when in contact with bodily fluids so as to release the encapsulated drugs.

In a further embodiment of the invention wherein the active ingredients comprise cationic surfactants, personal hygiene products, such as body lotions, moisturisers, creams and the like, can be provided by the present invention. The provision of such personal hygiene products employing an emulsion according to the present invention is desirable in that a combination of the well known moisturising properties of water in oil emulsions and the desirable skin feel properties of oil in water emulsions is achieved.

Aptly the inner phase comprises an aqueous solution of the active ingredient, wherein the solvent typically comprises water. The active ingredient is desirably present up to its limit of solubility, and in the case where aluminium chlorohydrate (which is a favoured ingredient) is employed as the active ingredient the former can be included in an amount of up to 80% by weight, based on the weight of the inner phase. It can be appreciated that the inclusion of the active ingredient up to its limit of solubility in the solvent of the aqueous phase is beneficial in allowing quantities of the active ingredient, which would otherwise be incompatible with the gelled outer phase, to be incorporated in the emulsion of the present invention.

Preferably a primary emulsion is initially formed wherein the aqueous solution of the active ingredient is dispersed within the non-aqueous phase. Desirably 45 to 85% by weight of the aqueous solution is dispersed in 15 to 55% by weight of the non-aqueous phase. Suitable 55 to 85% by weight of the primary emulsion is subsequently dispersed within a percentage balance by weight of an aqueous dispersion of a gellable material, such as gellan gum or the like.

A hydrophobic surfactant is generally included in the non-aqueous phase. Examples of suitable surfactants include cetyl dimethicone copolyol, polysorbate 60, sorbitan monolaurate, sorbitan monostearate, sorbitan mono-oleate, sorbitan monopalmate, sorbitan trioleate, polyethylene glycol-6-sorbitan beeswax, polyethylene glycol-20-sorbitan beeswax, ceteth-20-stearateath-2-steareath-20-oleath-2, aluminium magnesium hydroxidestearate and the like. Typically the surfactant is present at a level of 0.5 to 2.5% by weight, based on the weight of the non-aqueous phase. In the case where polysorbate 60 is employed, this surfactant is generally included at a level of 1.5 to 2.5% by weight, whereas cetyl dimethicone copolyol is typically employed at a level of 0.5 to 1.5% by weight.

A particularly preferred emulsion according to the present invention comprises an outer gelled phase comprising gellan gum, typically gelled by monovalent ions substantially as hereinbefore described, an intermediate phase comprising silicone oil and an aqueous inner phase containing an active cationic ingredient particularly aluminium chlorohydrate or aluminium-zirconium chlorohydrate. This particularly preferred emulsion is suitable for use as antiperspirant and there is further provided by the present invention an antiperspirant which comprises an emulsion comprising an outer gelled phase comprising gellan gum, an intermediate phase comprising silicone oil and an aqueous inner phase containing an active cationic ingredient selected from the group consisting of aluminium chlorohydrate and aluminium-zirconium chlorohydrate, wherein the inner phase containing the active cationic ingredient is encapsulated by the intermediate phase.

An anti-perspirant according to the present invention is generally a "stick" type anti-perspirant, whereby the emulsion is substantially solid. A "stick" type anti-perspirant as described herein typically comprises a substantially solid body of an emulsion according to the present invention configured to be received within a container, whereby the body is movable relative to the container between advanced and retracted positions.

There is still further provided by the present invention use of an anionic hydrocolloid substantially as hereinbefore described to provide a gelled outer phase of an emulsion, wherein the emulsion comprises a gelled outer phase comprising the anionic hydrocolloid, an intermediate non-aqueous phase and an aqueous inner phase containing an active ingredient incompatible with the gelled outer phase, whereby the inner phase containing the active ingredient is encapsulated by the intermediate phase.

There is further provided by the present invention a method of preparing an emulsion substantially as hereinbefore described, which method comprises dispersing, in a non-aqueous phase, an aqueous phase containing an active ingredient, so as to produce a primary two phase emulsion, mixing the primary emulsion with an aqueous dispersion of a gellable material and effecting gelation thereof.

Aptly the gellable material comprises one or more anionic hydrocolloids substantially as hereinbefore described, wherein the employ of gellan gum is particularly preferred. Similarly the non-aqueous phase and the active ingredient are substantially as hereinbefore described, wherein preferably the non-aqueous phase comprises a volatile silicone oil and the active ingredient comprises a cationic material incompatible with the anionic hydrocolloid.

Desirably a hydrophobic surfactant, such as cetyl dimethicone copolyol as described above, is intimately mixed with the non-aqueous phase prior to dispersal of the first mentioned aqueous phase therein. The employ of such a surfactant is beneficial in achieving stabilisation of the primary two phase emulsion.

Advantageously the non-aqueous phase is initially subjected to relatively low energy and shear agitation, typically employing a stirrer, such as a paddle stirrer or the like, stirring at a speed in the range of 350 to 450 rpm (preferably 390 to 410 rpm), during addition of the aqueous phase thereto.

Subsequently agitation of relatively high energy and shear is employed, typically stirring at a speed in the range of 1400 to 1600 rpra, preferably 1480 to 1520 rpm, whereby a stable primary emulsion is formed.

Typically the primary emulsion is heated to a temperature in the range of 50° to 60° C. prior to mixing with an aqueous dispersion of a gellable material.

Suitably the method involves dispersing a gellable material, typically the anionic hydrocolloid as hereinbefore described, in an aqueous carrier such as water, prior to mixing with the primary emulsion. The resulting aqueous dispersion is generally heated to a temperature in the range of 80 to 90° C. to effect hydration followed by addition of DEA cetyl phosphate or other similar surfactant as hereinbefore described. Aptly the dispersion is cooled to a temperature in the range of 50 to 60° C. prior to mixing with the primary emulsion. Optionally the mixture achieved on mixing the primary emulsion with the aqueous dispersion may be subjected to further heating to a temperature in the range of 65 to 70° C.

Gelation is desirably achieved by addition of gelling cations, typically monovalent ions such as potassium or sodium in the case where gellan gum is employed as the anionic hydrocolloid. Aptly the mixture is allowed to cool and set to form a gel. According to a preferred aspect of the invention tripotassium citrate is employed.

The weight percentages of the aqueous and nonaqueous phases, gelling cations and the like is substantially as hereinbefore described. Similarly the method may optionally further include blending ingredients, such as a fragrance, preservative or the like, as hereinbefore described, with the aqueous dispersion of the gellable material.

The present invention will now be illustrated by the following examples, which are for illustrative purposes only.

Example 1

|  | % w/w |
|---|---|
| Part A | |
| Polysorbate 60 | 2.0 |
| Aluminium-zirconium chlorohydrate (50% aqueous solution) | 49.0 |
| Silicone oil | 49.0 |
| Part B | |
| Gellan gum | 0.6 |
| Biocide (triclosan) | 2.0 |
| Deionised water | 95.4 |
| Polyethoxylated hydrogenated castor oil (60 ethylene oxide groups) | 2.0 |

Part A was prepared by initially blending the polysorbate 60 with the silicone oil. The aluminiumzirconium chlorohydrate was subsequently slowly added (by burette) whilst stirring at 400 rpm (±5 rpm) using a paddle stirrer, followed by stirring at 1500 rpm for 3–4 minutes to form a primary water in oil emulsion. The resulting primary emulsion was heated to 55° C. prior to intimately mixing with Part B.

Part B was prepared by dispersing the gellan gum in water, heating to 85° C. to effect hydration of the gellan gum, followed by addition of the polyethoxylated hydrogenated castor oil and biocide thereto and cooling to 55° C. for mixing with the primary emulsion of Part A.

50 parts by weight of the primary emulsion of Part A were mixed with 50 parts by weight of Part B whilst stirring at 800 rpm, followed by heating to 65–70° C. 0.5 parts by weight of $CaCl_2.6H_2O$ (0.1M) were added to gel the gellan gum, whereby gelation occurred on cooling.

Example 2

|  | % w/w |
| --- | --- |
| Part A |  |
| Cetyl dimethicone copolyol | 1.0 |
| Silicone oil | 20.0 |
| Aluminium chlorohydrate (50% aqueous solution) | 79.0 |
| Part B |  |
| Gellan gum | 1.0 |
| DEA cetyl phosphate | 2.0 |
| Biocide (triclosan) | 0.6 |
| Deionised water | 96.4 |

Part A was prepared by dissolving the cetyl dimethicone copolyol in the silicone oil. The aluminium chlorohydrate was subsequently slowly added (by burette) whilst stirring at 400 rpm (±5 rpm) using a paddle stirrer, followed by stirring at 1500 rpm for 3–4 minutes to form the primary water in oil emulsion. The resulting primary emulsion was heated to 55° C. prior to intimately mixing with Part B.

Part B was prepared by dispersing the gellan gum in water, heating to 85° C. to effect hydration of the gellan gum, followed by addition of the DEA cetyl phosphate and the biocide thereto and cooling to 55° C. for mixing with the primary emulsion of part A.

67 parts by weight of the primary emulsion of Part A were added to 33 parts by weight of Part B, whilst stirring at 800 rpm, followed by heating to 65–70° C. Tripotassium citrate was added to gel the gellan gum, whereby gelation occurred on cooling.

We claim:

1. A W/O/W sustained release emulsion comprising an aqueous gelled outer phase comprising one or more anionic hydrocolloids in an amount of 0.1% to 5% by weight of the weight of the outer phase, a non-aqueous intermediate phase comprising an oil and an inner phase containing a cationic ingredient incompatible with the gelled outer phase, wherein the inner phase containing the active ingredient is encapsulated by the intermediate phase.

2. An emulsion according to claim 1, wherein the anionic hydrocolloids comprise gellan gum, alginate, pectins, carrageenans, agar, or locust bean gum.

3. An emulsion according to claim 2, wherein the anionic hydrocolloid comprises gellan gum.

4. An emulsion according to claim 3, wherein the gellan gum is gelled by monovalent cations.

5. An emulsion according to claim 4, wherein the non-aqueous intermediate phase comprises an oil phase comprising silicone oil.

6. An emulsion according to claim 5, wherein the active ingredient comprises a cationic ingredient incompatible with the anionic hydrocolloid of the outer phase.

7. An antiperspirant comprising a W/O/W sustained release emulsion comprising a gelled outer phase comprising gellan gum, an intermediate phase comprising silicone oil and an aqueous inner phase containing an active cationic ingredient selected from the group consisting of aluminium chlorohydrate and aluminium-zirconium chlorohydrate, wherein the inner phase containing the active cationic ingredient is encapsulated by the intermediate phase.

8. A sustained release drug system comprising an emulsion according to any of claims 1, 2 or 3–6, comprising a cationic drug in an aqueous inner phase encapsulated by an intermediate oil phase, dispersed in an outer gel phase which is erodible when in contact with body fluids to release said encapsulated drug.

9. A personal hygiene product comprising an emulsion according to any of claims 1, 2 or 3–6, wherein the active ingredient comprises cationic surfactants, moisturizers or creams.

10. A method of preparing an emulsion according to any of claims 1, 2 or 3–6, which method comprises dispersing, in a non-aqueous phase, an aqueous phase containing an active ingredient, so as to produce a primary emulsion, mixing the primary emulsion with an aqueous dispersion of a gellable material and effecting gelation thereof.

11. A method according to claim 10, wherein 45 to 85% by weight of an aqueous solution of the active ingredient is dispersed in 15 to 55% by weight of the non-aqueous phase to form the primary emulsion, and 55 to 85% by weight of the primary emulsion is subsequently dispersed within a percentage balance by weight of the aqueous dispersion of the gellable material.

* * * * *

UNITED STATES PATENT AND TRADEMARK OFFICE
CERTIFICATE OF CORRECTION

PATENT NO. : 6,110,473
DATED : August 29, 2000
INVENTOR(S) : John Fitzpatrick et al.

It is certified that error appears in the above-identified patent and that said Letters Patent is hereby corrected as shown below:

COVER PAGE:

At Item [56] under "References Cited", insert the following:

--U.S. PATENT DOCUMENTS:

| | | | |
|---|---|---|---|
| 4,563,366, | 1/86, | Baird et al | 426/573 |
| 4,673,570, | 6/87, | Soldati | 424/66 |
| 4,803,195, | 2/89, | Holzner | 512/4 |
| 4,857,506, | 8/89, | Tyle | 514/12 |
| 4,985,250, | 1/91, | Bee et al | 424/401 |
| 5,258,184, | 11/93, | Bee et al | 424/401 |
| 5,306,498, | 4/94, | Vesperini et al | 424/401 |
| 5,332,809, | 7/94, | Della Valle et al | 536/119 |

FOREIGN PATENT DOCUMENTS:

62-125850, 6/87, Japan
63-267361, 11/88, Japan
2219803, 12/89, United Kingdom--.

Column 2:
Line 29, "iarman et al." should read --Jarman et al.--

UNITED STATES PATENT AND TRADEMARK OFFICE
CERTIFICATE OF CORRECTION

PATENT NO. : 6,110,473
DATED : August 29, 2000
INVENTOR(S) : John Fitzpatrick et al.

It is certified that error appears in the above-identified patent and that said Letters Patent is hereby corrected as shown below:

Column 3:
Line 8, "Weigh," should read --weight,--;

Column 5:
Line 66, "stabillisation" should read --stabilization--.

Column 6:
Line 9, "1600 rpra," should read --1600 rpm,--

Column 8:
Line 29, "claims 1, 2, 0r 3-6," should read --claims 1 to 6,--;
Line 33, "claims 1, 2, or 3-6," should read --claims 1 to 6,--;
Line 36, "claims 1, 2, or 3-6," should read --claims 1 to 6,--.

Signed and Sealed this

Twenty-sixth Day of June, 2001

*Attest:*

*Attesting Officer*

NICHOLAS P. GODICI
*Acting Director of the United States Patent and Trademark Office*